United States Patent [19]
Davis, Jr.

[11] Patent Number: 5,916,190
[45] Date of Patent: *Jun. 29, 1999

[54] BANDAGE FOR WRAPPING AN AMPUTEE'S STUMP

[76] Inventor: Leonard L. Davis, Jr., 15 South Jefferson Rd., Mexico, Mo. 65265

[*] Notice: This patent issued on a continued prosecution application filed under 37 CFR 1.53(d), and is subject to the twenty year patent term provisions of 35 U.S.C. 154(a)(2).

[21] Appl. No.: 08/674,673

[22] Filed: Jul. 2, 1996

[51] Int. Cl.⁶ .................................................. A61F 13/00
[52] U.S. Cl. .............................. 602/41; 602/53; 602/26; 602/61
[58] Field of Search ................... 602/41, 53, 61, 602/62, 64–66, 26, 27; 623/33–36; 128/876

[56] References Cited

U.S. PATENT DOCUMENTS

| | | |
|---|---|---|
| 2,243,422 | 5/1941 | Hollander et al. . |
| 2,484,130 | 10/1949 | Thibault .................................... 602/65 |
| 3,508,544 | 4/1970 | Moore et al. ............................. 602/65 |
| 3,529,597 | 9/1970 | Fuzak . |
| 3,971,374 | 7/1976 | Wagner . |
| 3,989,041 | 11/1976 | Davies . |
| 4,345,590 | 8/1982 | Nakajima . |
| 4,644,946 | 2/1987 | Cremona-Bonato . |
| 4,693,241 | 9/1987 | Trznadel . |
| 4,875,476 | 10/1989 | Garcia ........................................ 602/65 |
| 5,108,455 | 4/1992 | Telikicherla .............................. 623/33 |
| 5,127,898 | 7/1992 | McConnelll . |
| 5,183,460 | 2/1993 | Scherz ....................................... 604/41 |
| 5,221,252 | 6/1993 | Caprio et al. ............................. 602/26 |
| 5,314,496 | 5/1994 | Harris et al. .............................. 602/61 |
| 5,417,647 | 5/1995 | Down ........................................ 602/26 |
| 5,507,722 | 4/1996 | Richardson ............................... 602/61 |
| 5,538,500 | 7/1996 | Peterson ................................... 602/26 |
| 5,613,943 | 3/1997 | Palumbo ................................... 602/26 |
| 5,620,413 | 4/1997 | Olson ........................................ 602/65 |
| 5,755,679 | 5/1998 | Selner et al. .............................. 602/27 |

*Primary Examiner*—Mark O. Polutta
*Attorney, Agent, or Firm*—Senniger, Powers, Leavitt & Roedel

[57] ABSTRACT

A bandage for wrapping an amputee's stump to reduce the potential for swelling and deformation of the stump after amputation. The bandage includes an elongate wrap, at least one strip attached to the wrap and means for releasably fastening the wrap around the stump. The wrap has a length sufficient to wrap around the stump and a resilience sufficient to retain the bandage adjacent an end of the stump when the wrap is stretched around the stump. The strip extends laterally outward from the wrap. The strip has a width generally equal to the diameter of the stump and a length sufficient to wrap around the end of the stump when the wrap is wrapped around the stump adjacent the end of the stump. The strip is sufficiently resilient to compress the stump to reduce the potential for swelling and deformation of the stump when the strip is stretched around the end of the stump.

17 Claims, 2 Drawing Sheets

BANDAGE FOR WRAPPING AN AMPUTEE'S STUMP

BACKGROUND OF THE INVENTION

This invention relates generally to a bandage. More particularly, this invention relates to a bandage for wrapping the stump of an amputee to reduce swelling and deformation of the stump after amputation.

After partial amputation of a limb, it is frequently necessary to apply pressure to the stump to prevent it from swelling and deforming and to compress it to properly fit in a prosthesis. Accordingly, in the past, the stump has been wrapped in elastic bandages such as Ace® elastic bandages to apply pressure to the stump. (Ace is a federally registered trademark of Becton, Dickinson and Company of Paramus, N.J.) However, wrapping the stump with a conventional elastic bandage is difficult, particularly using only two hands, because numerous folds must be made and various sections of the bandage must be simultaneously held in place under tension as the bandage is wrapped around the stump. Further, conventional elastic bandages by their very nature frequently unwrap when positioned around the end of a stump, and amputees have difficulty re-wrapping the stump by themselves, thereby hampering the amputees' self-sufficiency.

In order to alleviate some of these problems, an elastic stocking has been developed which rolls onto the stump. The stocking is easier to apply than conventional elastic bandages and usually stays on more reliably, but it only applies sufficient pressure to the end of the stump when it is pulled tightly onto the stump against the end. However, pulling the stocking onto the stump is uncomfortable and even painful, particularly shortly after surgery. Moreover, different size stockings must be stocked to fit different size stumps, thereby increasing the cost of inventory.

Although other specialty appliances have been developed for compressing an amputee's stump, they have been unsuccessful because either they are difficult to apply or do not reliably stay in place. Further, the specialty appliances usually, are not economical to manufacture because of the quantity and non-standard sizes of material used in their construction or because of the complexity of the construction.

SUMMARY OF THE INVENTION

Among the several objects and features of the present invention may be noted the provision of a bandage adapted to reduce swelling and deformation of a stump after amputation and to compress the stump to properly fit it in a prosthesis; the provision of such a bandage which reliably stays in place on the stump; the provision of such a bandage which has a simple construction and is economical to manufacture; and the provision of such a bandage which is easily applied by one person.

Briefly, this invention involves a bandage for wrapping an amputee's stump to reduce the potential for swelling and deformation of the stump after amputation. The bandage comprises an elongate wrap having a length sufficient to wrap around the stump, at least one strip attached to the wrap extending laterally outward from the wrap, and means for releasably fastening the wrap around the stump. The wrap is sufficiently resilient to retain the bandage adjacent an end of the stump when the wrap is stretched around the stump. The strip has a width generally equal to the diameter of the stump and a length sufficient to wrap around the end of the stump when the wrap is wrapped around the stump adjacent the end of the stump. The strip is sufficiently resilient to compress the stump to reduce the potential for swelling and deformation of the stump when the strip is stretched around the end of the stump.

A second aspect of the invention involves a method of applying a bandage to an amputee's stump to reduce the potential for swelling and deformation of the stump after amputation. The method comprises the step of positioning the stump on the wrap so the wrap extends laterally outward from the stump adjacent the end of the stump and so the strip extends generally longitudinally outward from the stump from a position below the stump. The method further includes the steps of stretching the strip around the end of the stump so a portion of the strip lies above the stump, and wrapping the wrap around the stump and the portion of the strip lying above the stump under a sufficient tension to stretch the wrap around the stump. In addition, the method comprises the steps of fastening the wrap to prevent the wrap from unwrapping, and applying an adhesive between the wrap and stump to retain the bandage adjacent the end of the stump.

Other objects and features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
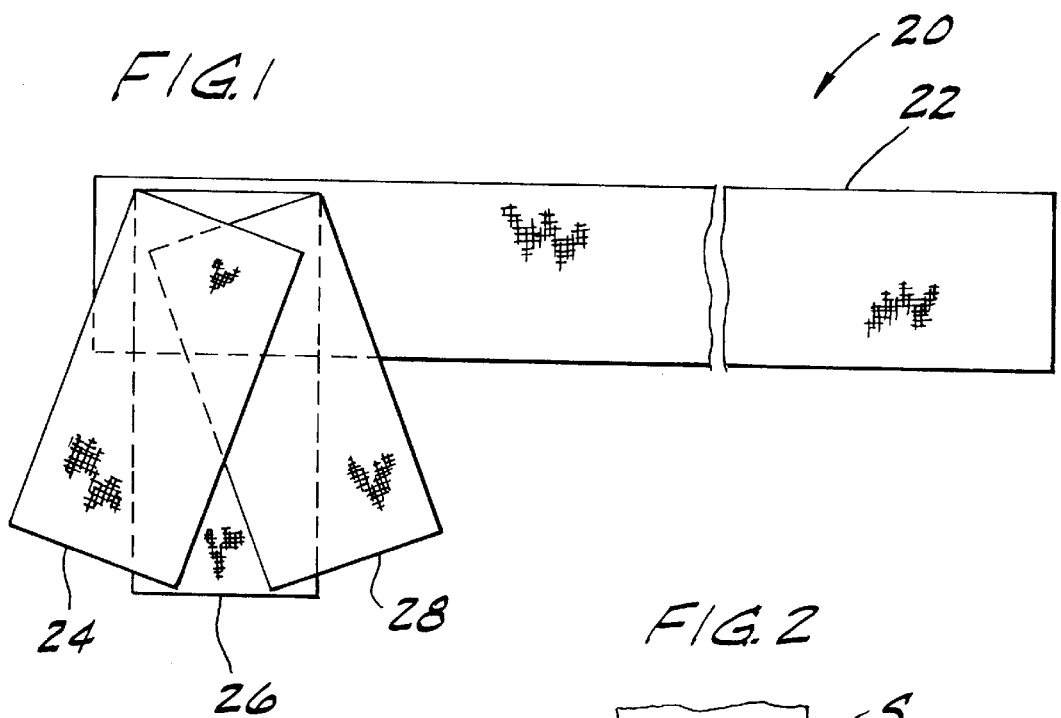
FIG. 1 is a partial top plan of the bandage of the present invention.

Referring now to the drawings and in particular to FIG. 1, the bandage of the preferred embodiment is indicated generally at 20. The bandage 20 comprises a wrap 22 having three strips 24, 26, 28 attached to the wrap adjacent one end. Depending upon the particular application, the wrap 22 and strips 24, 26, 28 will have differing dimensions; however, in the preferred embodiment of the bandage 20 used for wrapping the stump S (FIGS. 2–7) of an above-the-knee amputee, the wrap 22 is an Ace® elastic bandage approximately three feet long and four inches wide, and each of the three strips 24, 26, 28 is an Ace® bandage 24, 26, 28 approximately nine inches long and four inches wide. Regardless of the particular application, in the most preferred embodiment, the strips 24, 26, 28 have a width approximately equal to the diameter of the stump S to be wrapped.

The strips 24, 26, 28 may be attached to the wrap 22 using conventional attachment means such as sewing, rivets, staples, Velcro® fasteners, adhesives or the like. (Velcro® is a registered trademark of E.I. du Pont de Nemours and Company of Wilmington, Del.) Preferably, the attachment means permit the bandages to stretch in the vicinity of the attachment, but inextensible attachment means may also be used without departing from the scope of the present invention. The strips 24, 26, 28 of the preferred embodiment are attached adjacent one end of the wrap 22 as shown in FIG. 1. However, other strip attachment positions, such as intermediate the ends of the wrap 22, are also envisioned as being within the scope of this invention. In addition, strips 24, 26, 28 are attached to the wrap 22 so they are adjacent the end of the stump S when the wrap is wrapped around the stump S adjacent the end of the stump. This position tends to keep strips 24, 26, 28 in place on the end of the stump S rather than allowing them to slip off to the side of the stump. As shown in FIG. 1, strips 24, 26, 28 partially overlap one another in a fan-shaped configuration with strip 26 lying immediately adjacent wrap 22 and extending generally perpendicularly to the wrap. Strips 24 and 28 are obliquely angled with respect to the wrap 22 and strap 26. Each of the oblique strips 24, 28 is angled between ten and thirty degrees to either side of strip 26 and more preferably approximately twenty degrees to either side of strip 26 as shown in FIG. 1.

The bandage 20 of the present invention may be made by cutting an elastic bandage in desired lengths and processing the cut ends so they will not fray. Methods of processing the ends to prevent fraying include sewing the ends and applying polymeric coatings. The lengths of elastic bandage are positioned as shown in FIG. 1 and attached to one another using conventional attachment means to complete the bandage 20. As previously mentioned, the attachment means used to attach the lengths of bandage may include sewing, rivets, staples, Velcro® fasteners, adhesives or the like. It will be appreciated from the previous description that the bandage 20 of the present invention is both simple and inexpensive to manufacture.

Figure 2:
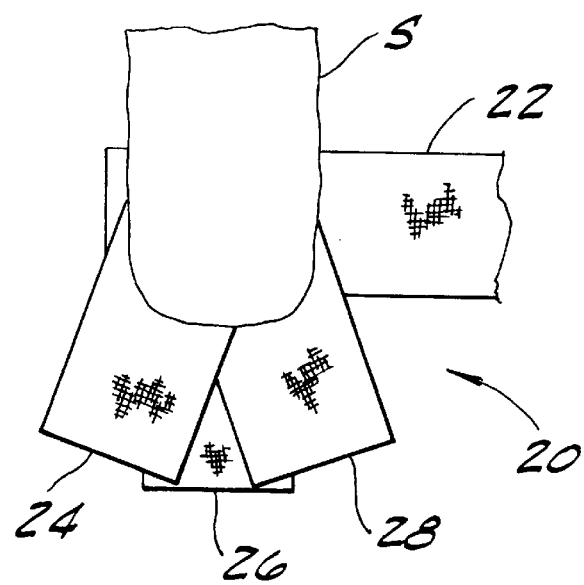
FIG. 2 is a partial top plan of a stump resting on the bandage prior to wrapping the stump.
Figure 3:
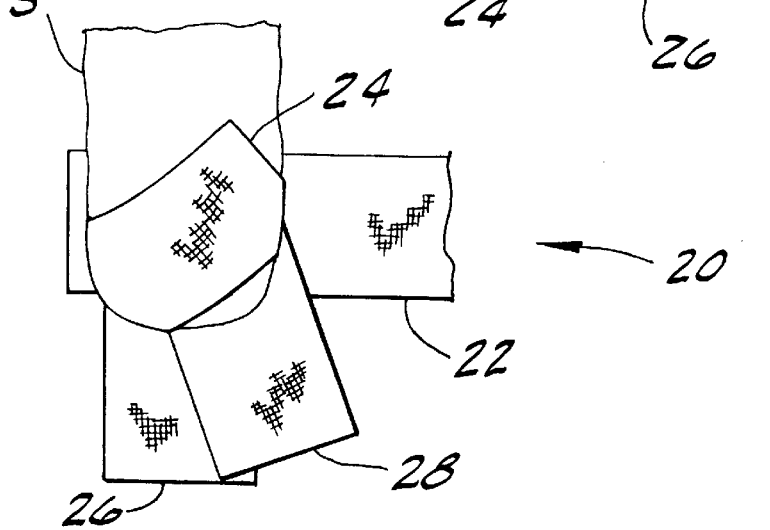
FIG. 3 is a partial top plan of the stump and bandage showing an oblique strip wrapped around an end of the stump.
Figure 4:
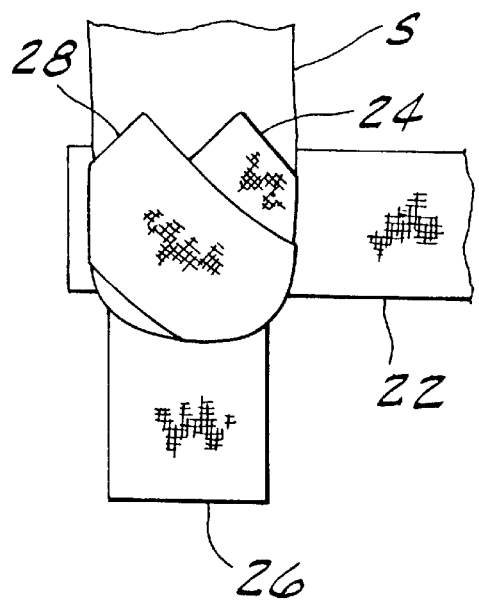
FIG. 4 is a partial top plan of the stump and bandage showing a second oblique strip wrapped around the end of the stump.
Figure 5:
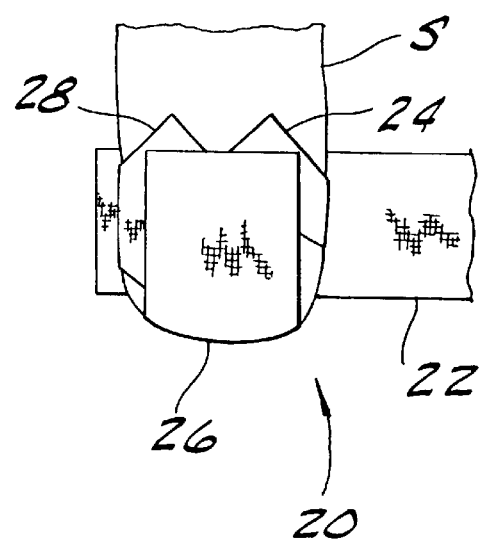
FIG. 5 is a partial top plan of the stump and bandage showing all of the strips wrapped around the end of the stump.
Figure 6:
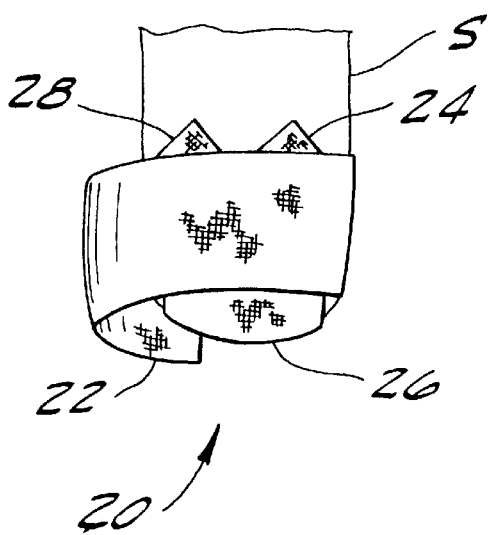
FIG. 6 is a partial top plan of the stump and bandage showing the wrap wrapped around the stump and all of the strips.
Figure 7:
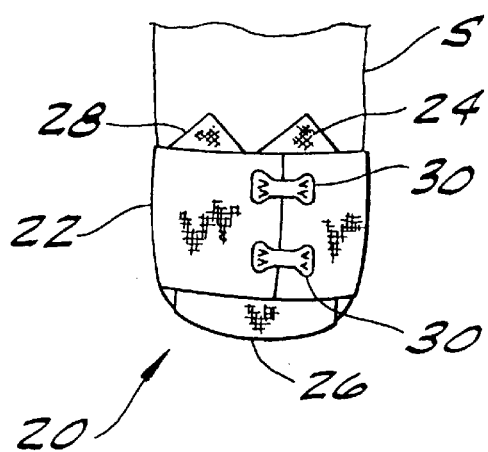
FIG. 7 is a partial top plan of the stump and bandage showing the bandage fastened in place around the stump.

To use the bandage 20 of the present invention, spray adhesive is applied to the surface of either the stump S, the bandage 20 or both to make the surface(s) tacky so the bandage will stay in place adjacent the end of the stump once applied. The bandage 20 is laid flat with the wrap 22 underneath the strips 24, 26, 28 and the amputee's stump S is positioned on top of the bandage so the wrap is adjacent the end of the stump and extends laterally outward from one side of the stump and so the strip 26 extends generally longitudinally outward from the end of the stump as shown in FIG. 2. Strip 24 is stretched around the end of the stump S so a portion of the strip lies above the stump and the strip is snug around the end of the stump S as shown in FIG. 3. Next, strip 28 is stretched around the end of the stump S so a portion of strip 28 lies above the stump and strip 24 as shown in FIG. 4. Strip 28 is also pulled so it is snug around the end of the stump S and so it bears against strip 24 so both strips may be simultaneously held in place with one hand. With the bandage 20 so positioned, strip 26 is stretched around the end of stump S as shown in FIG. 5. Strip 26 is pulled snugly around the end of the stump S so it bears against strips 24 and 28 so all of the strips may be held in place with one hand while the wrap 22 is wrapped around the stump S and the strips as shown in FIG. 6. The wrap 22 is stretched around the stump S so it is in tension and so the strips 24, 26, 28 and the bandage 20 itself are firmly held in place by the resilience of the wrap. Any one of several different types of means for releasably fastening elastic bandages such as metal clasps 30, safety pins, Velcro® fasteners, or adhesive tape may be used to fasten the wrap 22 in place around the strips 24, 26, 28 to prevent the wrap from unwrapping. Thus applied and fastened, the bandage 20 is held in position adjacent the end of the stump S as shown in FIG. 7.

The resiliency of the bandage 20 applies pressure to the stump S to reduce swelling and deformation of the stump after amputation. In addition, the resiliency compresses the stump S to mold it to a desired shape to improve the fit of a prosthesis (not shown) attached to the stump. Still further, the resiliency of the wrap 22 and spray adhesive act to hold the bandage 20 against the stump S so it stays in place and does not unwrap.

Minimizing the complexity of the bandage 20 and employing conventional elastic bandages and attachment means in the manufacture of the bandage reduces its overall cost, making the bandage very economical.

As is apparent from the description of its use above, the bandage of the present invention is easily applied by one person with only minimal dexterity. Thus, the amputee can apply the bandage 20 without the aid of medical staff thereby reducing medical costs and enabling the amputee to be more self-sufficient.

It will be apparent to those of ordinary skill in the art that additional fasteners may be added at various locations on the bandage 20 to aid in holding the components of the bandage together either during intermediate wrapping steps or after the bandage is wrapped. For instance, fasteners may be positioned between the strip 26 and wrap 22 to hold the strip 26 in position after the bandage is wrapped.

It will also be appreciated that portions of the bandage may be non-elastic without departing from the scope of the present invention. For instance, it is envisioned the wrap 22 or strips 24, 26, 28 may be formed from elastic segments positioned between non-elastic segments.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A bandage for wrapping an amputee's stump to reduce the potential for swelling and deformation of the stump after amputation, the bandage comprising:

an elongate wrap having a free end, a length sufficient to wrap around the stump and a width narrower than a length of the stump, the wrap being sufficiently stretchable and resilient to retain the bandage adjacent a distal end of the stump when the wrap is stretched around the stump;

at least one strip attached to the wrap in a non-parallel orientation and extending laterally outward from the wrap, the strip having a width generally equal to the diameter of the stump and a length sufficient to wrap over the distal end of the stump when the wrap is wrapped around the stump adjacent the distal end of the stump, the strip being sufficiently stretchable and resilient to compress the stump to reduce the potential for swelling and deformation of the stump when the strip is stretched over the distal end of the stump; and means for releasably fastening the wrap around the stump.

2. A bandage as set forth in claim 1 wherein the strip extends perpendicularly to the wrap.

3. A bandage as set forth in claim 2 wherein the strip is a first strip and the bandage further comprises a second strip extending obliquely with respect to the wrap and said first strip.

4. A bandage as set forth in claim 3 further comprising a third strip extending obliquely with respect to the wrap and said first and second strips.

5. A bandage as set forth in claim 4 wherein said first, second and third strips have substantially equal widths.

6. A bandage as set forth in claim 5 wherein said second and third strips are oriented at an angle of between ten and thirty degrees with respect to said first strip.

7. A bandage as set forth in claim 6 wherein said second and third strips are oriented at an angle of approximately twenty degrees with respect to said first strip.

8. A bandage as set forth in claim 7 wherein said first, second and third strips are positioned adjacent one end of the wrap.

9. A bandage as set forth in claim 8 wherein said first, second and third strips are attached to the wrap at a position on the wrap which is adjacent the end of the stump when the wrap is wrapped around the stump adjacent the end of the stump.

10. A bandage for wrapping an amputee's stump to reduce the potential for swelling and deformation of the stump after amputation, the bandage comprising:

an elongate wrap having a free end, a length sufficient to wrap around the stump and a width narrower than a length of the stump, the wrap being sufficiently stretchable and resilient to retain the bandage adjacent a distal end of the stump when the wrap is stretched around the stump;

at least one strip attached to the wrap in a non-parallel orientation and extending laterally outward from the wrap from a position on the wrap adjacent the distal end of the stump when the wrap is wrapped around the stump adjacent the distal end of the stump, the strip having a length sufficient to wrap over the distal end of the stump when the wrap is wrapped around the stump adjacent the distal end of the stump, the strip being sufficiently stretchable and resilient to compress the stump to reduce the potential for swelling and deformation of the stump when the strip is stretched over the distal end of the stump; and means for releasably fastening the wrap around the stump.

11. A bandage as set forth in claim 10 wherein the strip extends perpendicularly to the wrap.

12. A bandage as set forth in claim 11 wherein the strip is a first strip and the bandage further comprises a second strip extending obliquely with respect to the wrap and said first strip and wrap.

13. A bandage as set forth in claim 12 further comprising a third strip extending obliquely with respect to the wrap and said first and second strips.

14. A bandage as set forth in claim 13 wherein said second and third strips are oriented at an angle of between ten and thirty degrees with respect to said first strip.

15. A bandage as set forth in claim 14 wherein said second and third strips are oriented at an angle of approximately twenty degrees with respect to said first strip.

16. A bandage as set forth in claim 15 wherein said first, second and third strips are positioned adjacent one end of the wrap.

17. A bandage as set forth in claim 15 wherein said first, second and third strips have substantially equal widths.

\* \* \* \* \*